(12) United States Patent
Johannsen et al.

(10) Patent No.: US 7,802,483 B2
(45) Date of Patent: Sep. 28, 2010

(54) TEST DEVICE

(75) Inventors: Uwe Johannsen, Steinkirchen (DE);
Wolfram Schopenhauer, Hamburg (DE); Hilmar Peitz, Buchholz (DE); Cord Haack, Beckdorf (DE)

(73) Assignee: Airbus Deutschland GmbH (DE)

( * ) Notice: Subject to any disclaimer, the term of this patent is extended or adjusted under 35 U.S.C. 154(b) by 0 days.

(21) Appl. No.: 12/227,839

(22) PCT Filed: May 29, 2007

(86) PCT No.: PCT/EP2007/004730
§ 371 (c)(1),
(2), (4) Date: Nov. 25, 2008

(87) PCT Pub. No.: WO2007/137811
PCT Pub. Date: Dec. 6, 2007

(65) Prior Publication Data
US 2009/0090192 A1    Apr. 9, 2009

Related U.S. Application Data

(60) Provisional application No. 60/809,289, filed on May 30, 2006.

(30) Foreign Application Priority Data
May 30, 2006   (DE) .................. 10 2006 025 145

(51) Int. Cl.
*G01N 3/08* (2006.01)
(52) U.S. Cl. .................... 73/818; 73/862.391
(58) Field of Classification Search ..............
73/862.381–862.391, 802–818, 760, 856
See application file for complete search history.

(56) References Cited

U.S. PATENT DOCUMENTS

| | | | |
|---|---|---|---|
| 3,592,041 A | 7/1971 | Spencer | |
| 4,723,732 A | 2/1988 | Gorges | |
| 4,856,738 A | 8/1989 | Martin | |
| 4,936,527 A | 6/1990 | Gorges | |
| 6,293,585 B1 | 9/2001 | Bruns et al. | |
| 6,345,543 B1* | 2/2002 | Aoki | 73/862.474 |
| 7,185,727 B2* | 3/2007 | Mochizuki | 180/273 |
| 7,455,343 B2* | 11/2008 | Endo et al. | 296/68.1 |
| 7,625,010 B2* | 12/2009 | Fujii et al. | 280/801.1 |

(Continued)

FOREIGN PATENT DOCUMENTS

DE    198 10 641 C1    9/1999

(Continued)

OTHER PUBLICATIONS

"AC 25.562-1B", FAA Advisory Circular, [Online] Jan. 10, 2006, XP002451495.

*Primary Examiner*—Max Noori
(74) *Attorney, Agent, or Firm*—Lerner, David, Littenberg, Krumholz & Mentlik, LLP

(57) ABSTRACT

A test structure for dynamic seat tests comprises a load cell, a seat rail with a bar and a upper chord, a load transfer device, which comes into contact with opposite sides of the bar of the seat rail and is fixed to the load cell and an integrated floor plate which is fixed to the upper chord of the seat rail and to the load transfer device.

5 Claims, 1 Drawing Sheet

U.S. PATENT DOCUMENTS

Figure 1:
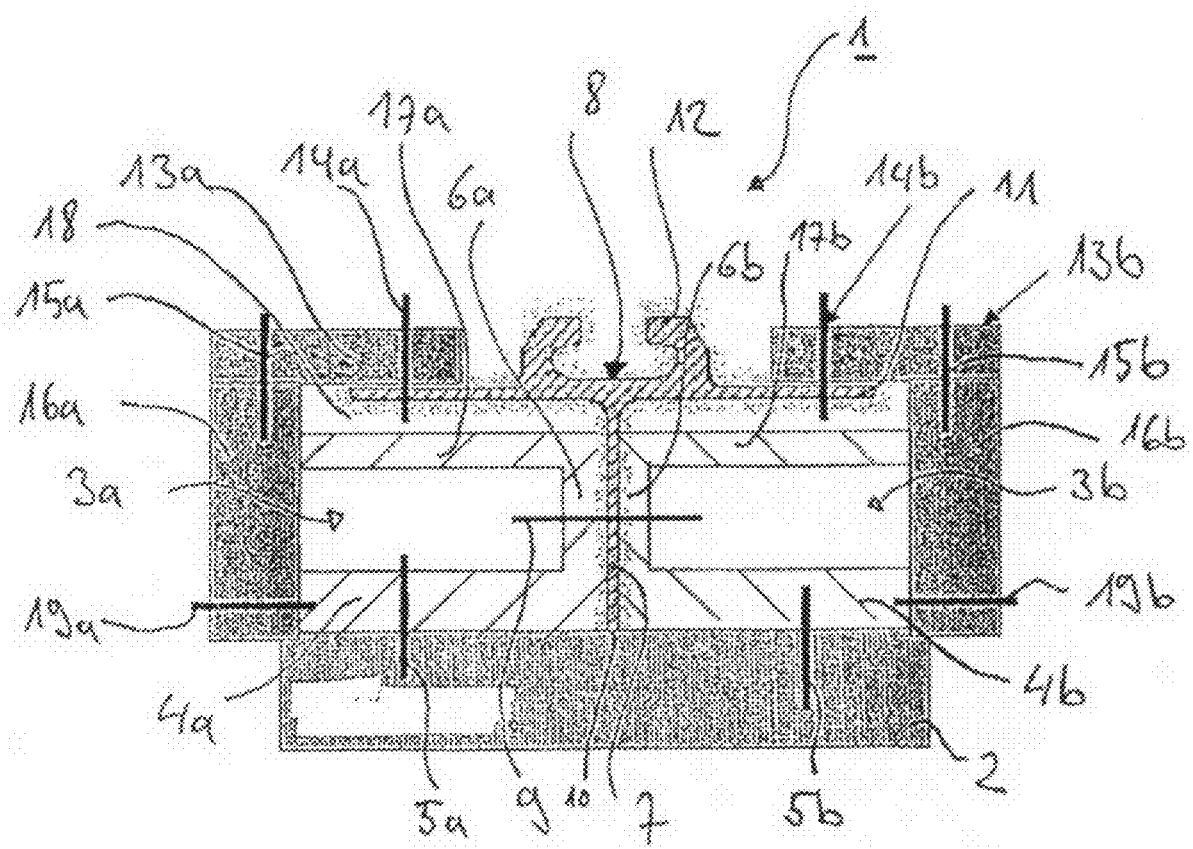

2002/0062699 A1    5/2002  Kimura
2003/0089530 A1*   5/2003  Paine ........................ 177/163

FOREIGN PATENT DOCUMENTS

| | | |
|---|---|---|
| DE | 103 10 653 A1 | 10/2004 |
| EP | 0 215 495 A2 | 3/1987 |
| EP | 0 282 244 A1 | 9/1988 |
| JP | 2002-166768 A | 6/2002 |
| JP | 2002-357492 A | 12/2002 |

* cited by examiner

TEST DEVICE

REFERENCE TO RELATED APPLICATION

This application claims the benefit of the filing date of German Patent Application No. 10 2006 025 145.8 filed May 30, 2006 and of U.S. Provisional Patent Application No. 60/809,289 filed May 30, 2006, the disclosures of which applications are hereby incorporated herein by reference.

FIELD OF THE INVENTION

The invention relates to a test device, in particular a test structure for dynamic seat tests in the aeronautics industry.

TECHNOLOGICAL BACKGROUND OF THE INVENTION

Due to increased seat weight, locally increased loads occur that need to be determined in an approval test with original seat rails by means of dynamic tests. In particular, the CS 25.562/FAR 25.562 conditions must be met.

The increase in the seat weight as a result of improved comfort for the passengers has resulted in a requirement for a significant improvement in the local load transfer.

SUMMARY OF THE INVENTION

There may be a need to provide a seating device for dynamic seat tests meeting the CS 25.562/FAR 25.562 conditions.

The achievement of the need is described in claim 1. Further developments of the invention are disclosed in the subordinate claims.

The test device according to the invention contains a load cell, a seat rail with a bar and an upper chord, a load transfer means which comes into contact with opposite sides of the bar of the seat rail and is fixed to the load cell, and a floor plate which is fixed to the upper chord of the seat rail and to the load transfer means.

According to a further development of the invention, the load transfer means comprises two profiles arranged on the opposite sides along the bar of the seat rail and fixed to these.

According to a further development of the invention, the profiles are U-profiles with limbs running parallel to the floor plate and extending outward away from the bar of the seat rail.

According to another further development of the invention, the aforementioned components, i.e., the upper chord, load transfer means, floor plate and load cell are each fixed by means of a screw, a clip and/or a groove.

For the local load transfer, according to the invention, in addition to the seat rail crown, the surrounding of the seat rail (floor plate) is also integrated in the test structure. This involves in particular the adaptation of floor plates, which are fixed with original fixing elements. The aim and result of the test device according to the invention is to increase the local load transfer into the seat rail by utilising the existing installation situation. This corresponds to the actual installation situation and results in a relatively higher load bearing capacity compared to known test structures.

In particular, the invention meets the so-called 10° roll (torsion) requirement in full.

DETAILED DESCRIPTION OF EXEMPLARY EMBODIMENTS

The following describes an example of an embodiment of the test device according to the invention with reference to the attached diagram.

FIG. 1 shows the test device 1 according to the preferred example of an embodiment. The test device 1 comprises a load cell 2 on which respective U-profiles 3a, 3b are arranged in such a way that respective limbs 4a, 4b of the U-profiles 3a, 3b come into contact with a surface of the load cell 2. The limbs 4a, 4b are fixed by means of fixing elements 5a, 5b, for example a screw, a clip, a groove, etc., to the load cell 2.

As shown in FIG. 1, the U-profiles 3a, 3b are arranged in such a way that a bar 7 of a seat rail 8 runs between their base regions 6a, 6b. The base regions 6a, 6b of the U-profiles 3a, 3b come into contact with the side surfaces of the bar 7 on a wide contact surface and are connected to each other by a fixing element 9, for example a screw, a clip, a groove, etc.

According to the preferred example of an embodiment, one frontal face 10 of the bar 7 comes into contact with the surface of the load cell 2, which is the same as that with which the limbs 4a, 4b of the U-profiles 3a, 3b come into contact.

The seat rail 8 is substantially T-shaped and comprises, on an end lying opposite to the frontal face 10 of the bar 7, an upper chord 11 extending substantially perpendicularly to the bar 7 and parallel to the surface of the load cell 2.

The seat rail 8 also comprises a crown 12, which is arranged substantially in the middle of the upper chord 11 symmetrical to the bar 7 in order to accommodate correspondingly designed components of a passenger seat (not shown). The crown 12, the upper chord 11 and the bar 7 of the seat rail 8 are preferably embodied in one piece but alternatively could also be embodied separately and welded to each other, for example.

As shown in FIG. 1, floor plates 13a, 13b are fixed by fixing elements 14a, 14b to the left and right of the crown 12 to the upper chord 11. The fixing elements 14a, 14b are for example a screw, a clip, a groove, etc, wherein the floor plates 13a, 13b are fixed to a surface of the upper chord 11 that is not facing the load cell 2.

As shown in FIG. 1, the floor plates 13a, 13b are fixed by fixing elements 15a, 15b to connecting elements 16a, 16b. The fixing elements 15a, 15b are for example a screw, a clip, a groove, etc.

The connecting elements 16a, 16b extend substantially parallel to the bar 7 from the floor plate 13a, 13b in the direction of the load cell 2.

As shown in FIG. 1, an interspace 18 is formed between the respective other limbs 17a, 17b of the U-profiles 3a, 3b.

The connecting elements 16a, 16b come into contact with the respective faces of the limbs 4a, 4b, 17a, 17b of the U-profiles 3a, 3b.

The connecting elements 16a, 16b are also fixed by fixing elements 19a, 19b via the respective faces to the limbs 4a, 4b of the U-profiles 3a, 3b. The fixing elements 19a, 19b are for example a screw, a clip, a groove, etc.

Although the above describes the invention with reference to a preferred example of an embodiment, it should be understood that that different modifications of the test structure are possible without leaving the scope of the invention as long as it is guaranteed that the local aircraft structure is integrated in the test structure.

In addition, the test device for dynamic seat tests is not restricted to the aeronautics industry but can also be used in other fields, for example the railway or shipping industries, etc.

The invention claimed is:
1. A test device, comprising
   a load cell;
   a substantially T-shaped seat rail with a bar and an upper chord;
   a load transfer device, which is arranged on the load cell and which comes into contact with opposite sides of the bar of the seat rail and is fixed on the load cell; and a floor plate, which is fixed to the upper chord of the seat rail and to the load transfer device.

2. The test device according to claim 1, wherein the load transfer device comprises two profiles which are arranged on the opposite sides along the bar of the seat rail and fixed thereto.

3. The test device according to claim 2, wherein the two profiles are U-profiles whose limbs run parallel to the floor plate and extend away from the bar of the seat rail.

4. The test device according to claim 1, wherein the floor plate is fixed by connecting elements to the load transfer device.

5. The test device according to claim 1, wherein the afixing of the upper chord, load transfer device, floor plate and load cell is implemented by at least one of a screw, a clip and a groove.

* * * * *

UNITED STATES PATENT AND TRADEMARK OFFICE
CERTIFICATE OF CORRECTION

| | | |
|---|---|---|
| PATENT NO. | : 7,802,483 B2 | |
| APPLICATION NO. | : 12/227839 | |
| DATED | : September 28, 2010 | |
| INVENTOR(S) | : Uwe Johannsen et al. | |

It is certified that error appears in the above-identified patent and that said Letters Patent is hereby corrected as shown below:

On the cover of the patent item (73) replace "Deuteschland" with --Deutschland--.

Signed and Sealed this
Fourth Day of October, 2011

David J. Kappos
*Director of the United States Patent and Trademark Office*